US012622758B2

(12) United States Patent
Bolsinger et al.

(10) Patent No.: US 12,622,758 B2
(45) Date of Patent: May 12, 2026

(54) CONSOLE FOR AN OPHTHALMIC SURGICAL SYSTEM FOR OPERATING A HANDPIECE, AND OPHTHALMIC SURGICAL SYSTEM

(71) Applicant: Carl Zeiss Meditec AG, Jena (DE)

(72) Inventors: Matthias Bolsinger, Bopfingen (DE); Caroline Kraft, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 564 days.

(21) Appl. No.: 18/316,835

(22) Filed: May 12, 2023

(65) Prior Publication Data

US 2023/0363835 A1 Nov. 16, 2023

(30) Foreign Application Priority Data

May 13, 2022 (DE) ..................... 10 2022 112 103.8

(51) Int. Cl.
| | |
|---|---|
| *A61B 34/00* | (2016.01) |
| *A61B 17/00* | (2006.01) |
| *A61F 9/007* | (2006.01) |

(52) U.S. Cl.
CPC .......... *A61B 34/25* (2016.02); *A61F 9/00736* (2013.01); *A61B 2017/00199* (2013.01); *A61B 2017/00535* (2013.01)

(58) Field of Classification Search
CPC .......... A61B 34/25; A61B 2017/00199; A61B 2017/00535; A61F 9/00736; A61F 9/00763; A61F 9/007
See application file for complete search history.

(56) References Cited

U.S. PATENT DOCUMENTS

| | | | |
|---|---|---|---|
| 8,728,108 | B2 | 5/2014 | Gao et al. |
| 2020/0179169 | A1 | 6/2020 | Agahi et al. |
| 2023/0201033 | A1 | 6/2023 | Agahi et al. |

FOREIGN PATENT DOCUMENTS

CN 113194894 A 7/2021

OTHER PUBLICATIONS

De Oliveira, P. R. C, et al, "Vitroretinal instruments: vitrectomy cutters, endoillumination and wide-angle viewing systems", International Journal of Retina and Vitreous, vol. 2, 28 (2016), pp. 1 to 36.

*Primary Examiner* — Cris L. Rodriguez
(74) *Attorney, Agent, or Firm* — Walter Ottesen, P.A.

(57) ABSTRACT

A console is for an ophthalmic surgical system for operating a handpiece driven by a work fluid. The work fluid is supplied to a respective work chamber depending on the switching states of work valves. The valves are switched between a switched-on state and a switched-off state by a respective drive unit by respective electrical switching signals being applied to the drive units. Each valve switches from the switched-off switching state into the switched-on switching state during a switch-on time delay and switches from the switched-on state to the switched-off state during a switch-off time delay. The switching signals at least intermittently adopt the switch-on electric potential concurrently during a difference time period if the switch-on delay is longer than the switch-off delay, with a length of time of the difference period arising on the difference between the switch-on delay and the switch-off delay of the valves.

11 Claims, 5 Drawing Sheets

CONSOLE FOR AN OPHTHALMIC SURGICAL SYSTEM FOR OPERATING A HANDPIECE, AND OPHTHALMIC SURGICAL SYSTEM

CROSS-REFERENCE TO RELATED APPLICATIONS

This application claims priority of German patent application no. 10 2022 112 103.8, filed May 13, 2022, the entire content of which is incorporated herein by reference.

TECHNICAL FIELD

The disclosure relates to a console for an ophthalmic surgical system for operating a handpiece which is drivable via a work fluid, with the handpiece being suitable in particular for use in an ophthalmic surgical method for treating an eye. The console includes a first work valve for applying the work fluid to a first work chamber of the handpiece depending on a switching state of the first work valve, with the first work valve including a first electric drive unit for switching the first work valve between a switched-on switching state and a switched-off switching state. Further, the console includes a second work valve for applying a work fluid to a second work chamber of the handpiece depending on a switching state of the second work valve, with the second work valve including a second electric drive unit for switching the second work valve between a switched-on switching state and a switched-off switching state. Each work valve is configured to switch from the switched-off switching state to the switched-on switching state during a switching-on time delay and to switch from the switched-on switching state to the switched-off switching state during a switching-off time delay. Moreover, the console includes a control unit which is electrically coupled to the first and to the second electric drive unit and which is configured to actuate the first and the second electric drive unit with respective first and second electrical switching signals such that a respective switching signal successively over time applies a switch-on electric potential for the switched-on switching state and a switch-off electric potential for the switched-off switching state to the respective electric drive unit. As a result, the work valves can in each case alternately adopt the switched-on and the switched-off switching state. Finally, the disclosure also relates to an ophthalmic surgical system having at least one handpiece which is drivable via a work fluid and which is suitable in particular for use in an ophthalmic surgical method for treating the eye. The handpiece includes a first and a second work chamber and a work piston which is movably arranged between the first and the second work chamber and to which the work fluid from the work chambers is able to be applied. Further, the ophthalmic surgical system includes a console for coupling the work chambers of the handpiece with the work fluid and for applying the work fluid to the chambers, and a work fluid source for providing the work fluid.

BACKGROUND

Generic methods, consoles and ophthalmic surgical systems are comprehensively known in the prior art, with the result that in principle there is no need for separate documentary evidence in this respect. They can be used, inter alia, for treatments of an eye, in particular of a human eye. However, the use is not restricted thereto. Treatment of an eye refers in particular to a treatment of a body with an eye-like consistency, for example a gel body, a tissue body which includes an at least partly elastic or flowable substance of high viscosity, an eye-like test body, a non-living eye, for example an eye taken from a human or animal body, and/or the like. By way of example, the gel body or the tissue body can be at least partly dimensionally stable. Moreover, provision can be made, for example, for the handpiece to be able to be used for treatment of the living eye. In particular, the handpiece can be suitably configured for a treatment of the living eye. The handpiece is preferably an ophthalmic surgical handpiece. Depending on type and application and/or requirement of the treatment, the handpiece is configured with appropriate adaptations, for example for treatment of the vitreous humor of the eye or else retina as a vitrectomy cutting tool (also referred to as a vitrectomy cutter), as a handpiece for phacoemulsification or the like.

For their intended use, the handpieces are coupled to the console which inter alia provides power and auxiliary and operating substances for the intended use. Vitrectomy cutting tools and their function are explained in, for example, "Vitreoretinal instruments: Vitrectomy-Cutters, Endoillumination and White-Angel-Viewing Systems" by Paolo Riccardo Javez de Olivera et al. in "International Journal of Retina and Vitreus", published on Dec. 5, 2016 in International Journal of Retina an Vitreus, 2021. For example, this document discloses a vitrectomy cutting tool which has a cutting blade that is driven mechanically via a work piston. The vitrectomy cutting tool includes a work cylinder having a first and a second work chamber, the work piston being movably arranged between the first and the second work chamber and, via the work chambers, being able to be impinged upon by the work fluid, which generally is formed by a fluid such as for example a gas, in particular air. For this purpose, the work fluid is alternately applied to the work chambers of the vitrectomy cutting tool so that the work piston is moved back and forth in accordance with the change of the application of the work fluid, for the purpose of realizing the cutting movement. In this context, U.S. Pat. No. 8,728,108 B2 further discloses systems and methods for dynamic-pneumatic valve drives.

Even though the prior art has proven its worth, there still is need for improvement. A cycle rate or else cutting rate that is as high as possible, in particular greater than approximately 10 000 cycles or cuts per minute (cpm) is desirable, especially in the case of a posterior vitrectomy. Although a high cycle rate can be achieved using vitrectomy cutting tools which—as explained—have a dual pneumatic drive, that is, have two work chambers acting on a work piston and consequently are based on the principle of a twice-acting cylinder, the drive for such a vitrectomy cutting tool must be configured to be able to provide two corresponding alternating pressure signals. What should be observed in this context is that a pressure difference between the two work chambers should be as high as possible since the work piston of the vitrectomy cutting tool, and hence also a blade of the cutting tool, moves in accordance with this pressure difference. In this case, it is further desirable to keep a pressure in the work fluid, especially in relation to the work fluid source, as low as possible as this may have an effect on the volume of the drive and vibrations of the vitrectomy cutting tool. A maximum possible cycle rate achievable with the vitrectomy cutting tool, that is, complete opening and closing of the vitrectomy device, is limited inter alia by the achievable pressure difference in relation to the work chambers. Further, this pressure difference depends, inter alia, on the pressure of the work fluid, switching time delays of the work valves, and a duty cycle in relation to the first and the second switching signal.

SUMMARY

It is an object of the disclosure to make available a console for an ophthalmic surgical system for operating a handpiece which is drivable via a work fluid, via which a high working speed is achievable. It is also an object of the disclosure to make available an ophthalmic surgical system having such a console.

The above object is, for example, achieved via a console for an ophthalmic surgical system for operating a handpiece which is drivable via a work fluid. The handpiece is suitable for use in an ophthalmic surgical method for treating an eye. The console includes: a first work valve for applying the work fluid to a first work chamber of the handpiece in dependence upon a switching state of the first work valve, the first work valve including a first electric drive unit configured to switch the first work valve between a switched-on switching state and a switched-off switching state; a second work valve for applying the work fluid to a second work chamber of the handpiece in dependence upon a switching state of the second work valve, the second work valve including a second electric drive unit configured to switch the second work valve between a switched-on switching state and a switched-off switching state; each of the first work valve and the second work valve being configured to switch from the switched-off switching state to the switched-on switching state during a switch-on time delay and to switch from the switched-on switching state to the switched-off switching state during a switch-off time delay; a control unit electrically coupled to the first electric drive unit and to the second electric drive unit and configured to actuate the first electric drive unit via a first electrical switching signal and the second electric drive unit via a second electrical switching signal such that a corresponding one of the first electrical switching signal and the second electrical switching signal successively over time applies a switch-on electric potential for the switched-on switching state and a switch-off electric potential for the switched-off switching state to a corresponding one of the first electric drive unit and the second electric drive unit so that the first work valve and the second work valve in each case alternately adopt the switched-on and the switched-off switching state, wherein in relation to a respective change of the switching states of the first work valve and the second work valve, the control unit is configured such that: the first electrical switching signal and the second electrical switching signal assigned to corresponding ones of the first work valve and the second work valve at least intermittently adopt the switch-on electric potential concurrently during a difference time period if the switch-on time delay of the first work valve and the second work valve is longer than the switch-off time delay of the first work valve and the second work valve, or the first electrical switching signal and the second electrical switching signal assigned to corresponding ones of the first work valve and the second work valve at least intermittently adopt the switch-off electric potential concurrently during the difference time period if the switch-on time delay of the first work valve and the second work valve is shorter than the switch-off time delay of the first work valve and the second work valve; and, wherein the length of time of the difference time period arises on a basis of a difference between the switch-on time delay of the first work valve and the second work valve and the switch-off time delay of the first work valve and the second work valve.

In relation to a generic console, the disclosure in particular proposes that in relation to a respective change of the switching states of the work valves, the control unit is configured so that the switching signals assigned to the work valves at least intermittently adopt the switch-on electric potential at the same time during a difference time period if the switch-on time delay of the work valves is longer than the switch-off time delay of the work valves, or so that the switching signals assigned to the work valves at least intermittently adopt the switch-off electric potential at the same time during the difference time period if the switch-on time delay of the work valves is shorter than the switch-off time delay of the work valves, with the length of time of the difference time period in each case arising on the basis of a difference between the switch-on time delay of the work valves and the switch-off time delay of the work valves.

As regards an ophthalmic surgical system of the type in question, the disclosure proposes in particular that the console is configured according to the disclosure.

The disclosure is based, inter alia, on the idea that, depending on the switching-time delays of the work valves, a temporal overlap of the first and the second switching signal in relation to the switched-on or switched-off switching state can enable a flow-technical lengthened switched-on switching state of the work valves in the case of the same cycle rate, with the result that this can provide the option of increasing the differential pressure and/or reducing the work fluid pressure, in particular on the part of the work fluid source. Moreover, this concept can also be used to further increase the cycle rate such that the use of the handpiece, in particular the use of the vitrectomy cutting tool, can be improved further. In so doing, the disclosure is able to provide these advantages without the need to interfere with the handpiece or the work valves with their drive units. All that is needed are measures in relation to the control unit, via which an appropriate temporal overlap of the switching signals can be achieved in a specified manner. In this case, the disclosure relates in particular to work valves in which the switch-on time delay is longer than the switch-off time delay. What can be achieved by the difference time period is that, in particular, the work valves substantially do not adopt the flow-technical switched-on switching state at the same time. Therefore, the difference time period can specify an upper limit for the temporal overlap of the switch-on potentials of the switching signals in relation to a respective change, in particular in relation to a change of a travel of the work piston. However, the disclosure is not restricted thereto and, in principle, can also be used in the reverse case, that is, if the switch-on time delay is shorter than the switch-off time delay. In this case, the switching signals of the work valves should simultaneously adopt the switch-off potential, at least during the difference time period. In the present case, the switching state of the work valve refers in particular to a flow-technical switching state, which relates to whether or not the work valve allows a passage of work fluid. What can be achieved in both cases is that each work valve can be in the flow-technical switched-on state for as long as possible within a period or within a cut cycle, and what can also be achieved at the same time is that the work valves are substantially not simultaneously in the switched-on switching state from a flow-technical point of view. The work fluid source can be provided at least in part by the console. However, the work fluid source can also at least in part be configured as an external work fluid source which, for example, may be formed separately from the console.

The switch-on time delay refers in particular to the period of time which starts at the time at which there is a change of the corresponding switching signal from the switch-off potential to the switch-on potential. This period of time ends at the time at which, as a consequence of the change in the switching signal, the work valve reaches the switched-on switching state from a flow-technical point of view. Accordingly, what applies to the switch-off time delay is that this refers in particular to a period of time which starts at the time at which the switching signal switches from the switch-on potential to the switch-off potential and which ends at the time at which the corresponding assigned work valve reaches the switched-off switching state from a flow-technical point of view. In the case of generic work valves, the switch-on time delay may for example range from approximately 1.5 ms to approximately 7 ms, preferably range from approximately 2 ms to approximately 5 ms, particularly preferably be of the order of approximately 4 ms. By way of example, the switch-off time delay of such a work valve may range from approximately 0.5 ms to approximately 3 ms, preferably be of the order of approximately 2 ms. However, this may also be different, depending on the structure of the work valve. Work valves for which the switch-on time delay is shorter than the switch-off time delay are also conceivable. Overall, the disclosure is advantageously usable if the work valves preferably used in the console for the purpose of controlling the handpiece are substantially approximately the same. However, the disclosure is not restricted thereto and can equally also be used if use is made of different work valves, especially in relation to the switching time delays. The disclosure allows the different switching time delays to be considered accordingly, and the determination of an appropriate difference time period. The difference time period and its application can be adapted specifically, in particular on an individual basis.

The work valve can preferably include the electric drive unit. In principle, although the electric drive unit can be provided as a separate unit in relation to the work valve and can be accordingly mechanically coupled to the latter such that the electric drive unit is able to actuate the work valve in relation to the adoption of the respective switching positions, the electric drive valve is preferably included by the work valve and by preference forms a structural unit with the latter.

The electric drive unit can preferably be in the form of an electromagnet which, for example in the style of a solenoid, includes an electric coil to which a current is able to be applied, with a preferably magnetizable armature being arranged in axially movable fashion within the coil. The armature is mechanically connected to a valve body of the work valve, with the result that, by way of the armature, the valve body can be moved between a position in which the valve body rests in sealing fashion against a valve seat of the work valve in order to provide the closed switching state of the work valve and a further state in which the valve body is positioned at a distance from the valve seat in order to provide the switched-on switching state of the work valve. The armature is moved between the respective positions on account of a magnetic force, with optionally a supplementary spring force being taken into account. For this purpose, the electric coil is actuated by the corresponding switching signal. The switching signal is an electrical signal which causes a corresponding current flow in the electric coil, with the result that the armature is moved as desired. However, the disclosure is not restricted to the use of an electromagnet. Other drive units may also be used, for example a piezo-based drive unit or the like. However, the drive unit is not restricted thereto. The drive unit could also be configured to have a capacitive effect. A corresponding electric current used to drive the drive unit having a capacitive effect could also be considered instead of the electric potentials in this case. In principle, the same considerations as were specified for the electric potentials apply in this case.

The switching signal time profiles are preferably formed by corresponding rectangular signals. Each switching signal of the two switching signals is adapted in terms of its electrical properties to the respective drive unit. This relates in particular to the switch-on electric potential and the switch-off electric potential, or to the corresponding potential difference as voltage. If the work valves and their associated drive units have essentially the same form, then the switch-on potential and the switch-off potential are generally also substantially the same for both switching signals. By way of example, the voltage between the switch-on electric potential and the switch-off electric potential can be a few volts, for example approximately 3 V to approximately 60 V, preferably approximately 5 V to approximately 24 V. However, the voltage can also be chosen to be larger or smaller if necessary.

The voltage of the switching signal can preferably be a pulsating DC voltage. For example, if the switch-on time delay of the work valves is longer than the switch-off time delay, then the disclosure allows the change in the first switching signal from the switch-off potential to the switch-on potential to be brought forward in time by a difference time period made up of the two switching-time delays, with the result that when the second work valve reaches the switched-off switching state from a flow-technical point of view, the first work valve can reach the switched-on switching state from a flow-technical point of view. A time overlap of the flow-technically switched-on switching states of the work valves can be avoided as a result of the difference time period. Thus, the disclosure makes it possible to bring the flow-technical switching states closer to one another, with the result that the respective switched-on flow-technical switching states of the flow valves can be lengthened. At the same time, this also allows the differential pressure to be increased or the cutting speed to be made faster.

As a result, a time overlap of the switch-on potentials for the two switching signals, for example, may naturally arise for the difference time period. Now, the control unit is configured accordingly, with the result that it correspondingly provides the switching signals on the basis of the switching time delays. For this purpose, provision can be made for the switching time delays of the control unit to be made available as a file. This file may have been created on the basis of data that were determined empirically for the work valves. Moreover, there naturally also is the option of the control unit itself being able to determine these switching time delays at least in part, by using further supplementary means such as sensors or the like.

The control unit can adopt or provide functions, in particular in relation to the control of the work valves, in particular in relation to the operation of the drive units, and/or the like. The control unit itself can be provided as a separate component. However, it is preferably a constituent part of the console and particularly preferably arranged integrated into the latter. In principle, the control unit can be configured, at least in part or else completely, as an electronic hardware circuit. Moreover, the control unit may be formed, at least in part or else in full, by a computer unit controlled via a suitable computer program in order to be able to provide the desired functionality.

According to an embodiment, it is proposed that the console is configured to drain the work fluid from a respective work chamber in the switched-off switching state of the respective assigned work valve. As a result, the corresponding work chamber can be unburdened of the work fluid, with the result that a corresponding movement of the work piston can be assisted. For example, the work fluid can be drained using a vacuum or a negative pressure from a negative pressure source. However, provision can also be made for the work fluid to merely be discharged into the surroundings. In this way, draining the work fluid can be effected particularly quickly, as a result of which it is also possible to further assist the provision of a large differential pressure. Work fluid drainage can be realized for example via a flow control device or the like, for example by virtue of the work fluid being able to be drained directly at the handpiece itself, especially if the work fluid is a gas.

The work fluid is preferably drained via the respective work valve. In the switched-off flow-technical switching state, the work valve may to this end provide a drainage channel or merely a drainage opening, via which it is possible to drain the work fluid. To this end, the work valve may provide a switch-over functionality which alternately connects the work chamber to the work fluid source in the flow-technical switched-on switching state and to the opening in the switched-off switching state. What can preferably be achieved in this way is that the function of draining the work fluid can be provided by way of the console so that no appropriate devices need to be provided on the part of the handpiece, as a result of which the structure and/or the operation of the handpiece can be improved, especially during the intended use of a treatment of the eye. This configuration is particularly suitable for use in a surgical setting.

Moreover, it is proposed that the work fluid is drained via a respective first or second release valve. In this configuration, the release valves are provided in addition to the work valves and are preferably actuated in complementary fashion in relation to the latter. The release valve is preferably in the flow-technical switched-on switching state when the work valve is in the flow-technical switched-off switching state. Further, the release valve is in the flow-technical switched-off switching state when the work valve is in the flow-technical switched-on switching state. The release valves can be controlled hydraulically, pneumatically or else electrically via a respective drive unit. They are preferably electrically controllable and, in particular, connected to the control unit so that they can be actuated by the control unit with respective appropriate switching signals.

According to an embodiment, provision can be made for the control unit to be configured to determine the length of time of the difference time period substantially independently of a frequency of the switching signals. What this configuration allows to take into account is that the respective switching delays may at least partly be substantially independent of the frequency of the switching signals or the actuations of the work valves. As a result, the difference time period need not be adapted, not even in the case of a variable frequency of the switching signals or cycle rate. What can be particularly preferably provided for this case is that the control unit is programmed with a difference time period which particularly preferably may be fixedly set. Additionally, no file containing the switching time delays of the work valves needs to be provided in this case. Rather, it is sufficient to accordingly specify the difference time period in the control unit, for example by way of an input at an input unit which is communicatively couplable to the control unit and on which for example a user can make an appropriate input or the like. As a result, the disclosure can be realized particularly easily. By contrast, if the switching delays are frequency-dependent, then this can be taken into account accordingly for the determination of the difference time period. The difference time period can then be accordingly frequency dependent.

According to a further embodiment, it is proposed that for the purpose of determining a switch-on time delay or switch-off time delay of a respective work valve, the control unit is configured to detect a handpiece-side pressure of the work fluid via a pressure sensor at the respective work valve. As a result of this development, it is possible to at least partly monitor the switch-on time delay or switch-off time delay of the work valves and—if necessary—accordingly adapt the length of time of the difference time period depending on the determined switching time delays. By way of example, the control unit may be capable of determining the switching delays itself. As a result, it is possible to respond accordingly to signs that the work valves are aging or else to possible frequency dependencies of the switching time delays of the work valves. The appropriate measures are preferably implemented outside of the intended operation of the ophthalmic surgical system. However, provision can also be made for appropriate data to be acquired and evaluated during the intended operation such that the control unit is capable of adapting the corresponding switching signals according to need, even during the intended operation. This allows a highly precise setting for a respective individual operating state to be obtained. The differential pressure can also be further increased as a result of this.

Moreover, it is proposed that the control unit is configured to detect via a position sensor at least one end position of a work piston movably arranged between the first and the second work chamber, and to additionally adjust the switching signals on the basis of the at least one detected end position. The position sensor is preferably arranged in the handpiece and can detect, preferably contactlessly, the respective end position of the work piston. Two opposing end positions of the work piston are particularly preferably detected. Detection can be implemented via light, electric and/or magnetic fields, or the like. This development allows the reaching of the end positions to be detected reliably, especially in the case of high cycle rates, and, should the desired end position not have been reached, the optional adaptation, for example increase, of the pressure of the work fluid, especially in relation to the work fluid source. This also allows the differential pressure to be further increased, with the result that, in combination with the at least intermittent temporal overlay of the switch-on potentials, the operation of the handpiece, in particular of the vitrectomy cutting tool, can further be improved. By way of example, the position sensor can detect the position of the piston via light, a magnetic field, an electric field, and/or the like. The position sensor has an appropriately adapted embodiment and is preferably connected to the control unit so that the control unit is able to evaluate the position signals provided by the position sensor.

According to an embodiment, it is proposed that the handpiece is a vitrectomy cutting tool and the control unit is configured to set a pressure of the work fluid on the basis of a cycle rate. What this can achieve is that the work pressure only needs to be chosen to be large whenever this is also required for the corresponding cycle rate. As a result of the option of being able to reduce the pressure of the work fluid, it is possible during intended operation to also accordingly reduce acoustic noise and vibrations, in particular of the console and/or of the vitrectomy cutting tool or of the drive unit thereof. As a result, the intended operation of the vitrectomy cutting tool can be further improved.

According to an embodiment, it is proposed that the handpiece is a vitrectomy cutting tool and the control unit is configured to additionally determine a duty cycle of the switching signals for a specified or specifiable cycle rate, at least on the basis of a period duration of the specified or specifiable cycle rate, a period duration of a maximum cycle rate, and the switch-on time delay or switch-off time delay of the work valves. As a result, it is possible overall to obtain an improved method implementation during the intended use. Preferably, the duty cycle (DC) can be determined as follows:

$$DC = 0.5 - \frac{T_{max} - (T_{on} + T_{off})}{T}$$

Here, $T_{max}$ denotes the period duration assigned to the maximum cycle rate, $T_{on}$ denotes the switch-on time delay, $T_{off}$ denotes the switch-off time delay and T denotes the desired specified or specifiable period duration. Preferably, this formula is particularly advantageously applicable if the two work valves have substantially the same embodiment.

The advantages and effects indicated for the method according to the disclosure are also equally applicable to the ophthalmic surgical system and the console of the ophthalmic surgical system, and vice versa. In particular, method features may therefore also be formulated as device features, and vice versa.

BRIEF DESCRIPTION OF DRAWINGS

The invention will now be described with reference to the drawings wherein.

DETAILED DESCRIPTION

In the figures, identical reference signs denote identical features and functions.

Figure 1:
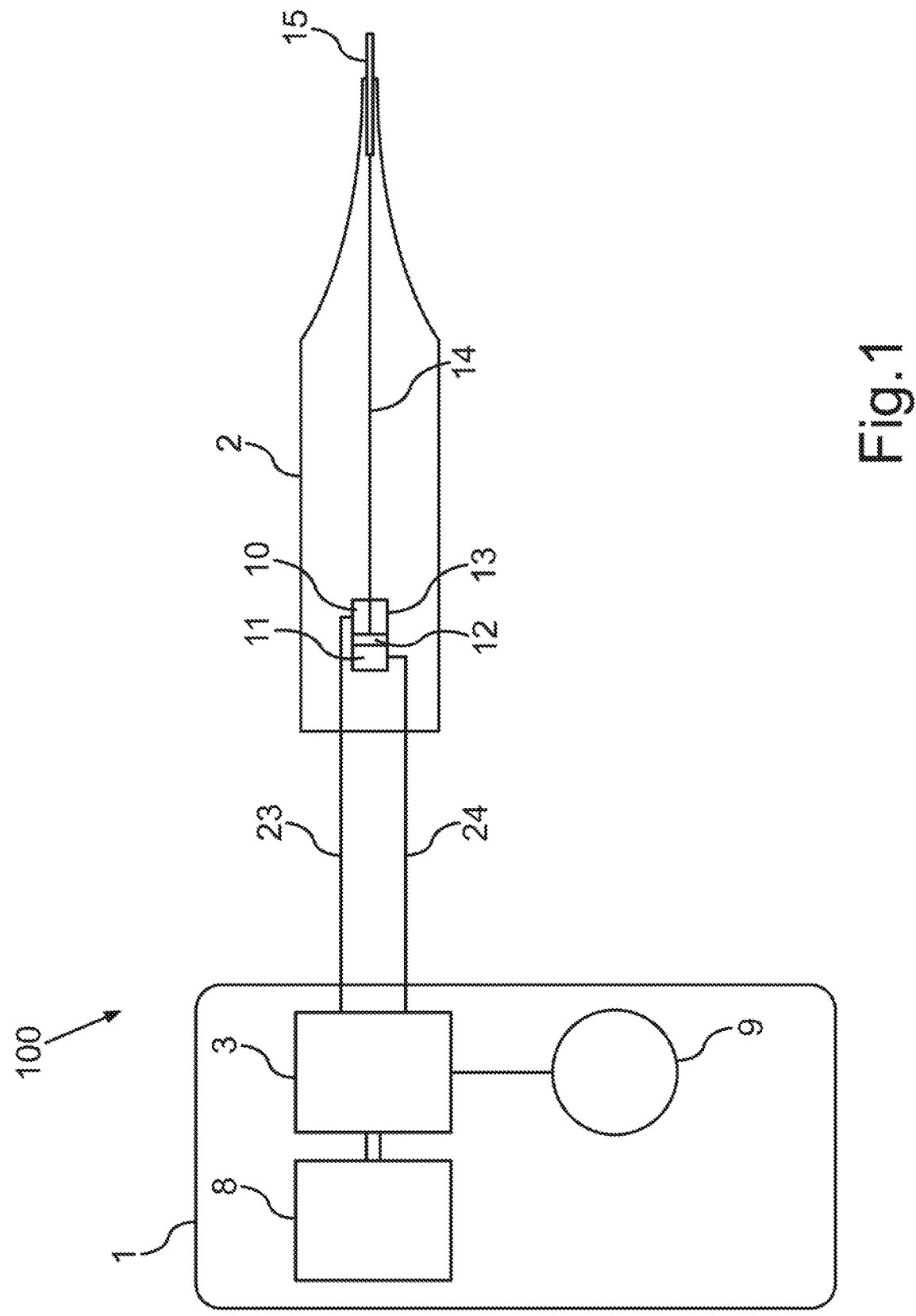
FIG. 1 shows a schematic illustration of an embodiment of an ophthalmic surgical system with a console, to which a vitrectomy cutting tool is connected.

FIG. 1 shows a schematic illustration of an ophthalmic surgical system 100 having a console 1, to which a vitrectomy cutting tool 2 as a handpiece is connected. The ophthalmic surgical system 100 is a medical treatment system which serves to treat an eye (not illustrated). The console 1 of the ophthalmic surgical system 100 serves to connect and operate the vitrectomy cutting tool 2 during intended operation, in particular during the treatment of the eye. The vitrectomy cutting tool 2 includes a cutting unit 15 which is connected via a drive rod 14 of the vitrectomy cutting tool 2 to a drive piston 12 of the vitrectomy cutting tool 2. During intended operation, the drive piston 12 is moved back and forth—as explained below —, so that the cutting unit 15 is also actuated accordingly via the drive rod 14, in order to be able to carry out the desired cuts. A person skilled in the art is aware of the function of the vitrectomy cutting tool 2, and this is why detailed explanations in this respect can be omitted here.

The drive piston 12 is movably mounted within a work cylinder 13 of the vitrectomy cutting tool 2. The drive piston 12 divides an unlabeled interior of the work cylinder 13 into a first work chamber 10 and a second work chamber 11. During intended operation, compressed air as a work fluid is usually applied alternately to the work chambers 10, 11, with the result that the drive piston 12 moves back and forth within the work cylinder 13 and is consequently able to drive the cutting unit 15 via the drive rod 14.

The console 1 includes a valve unit 3, which is coupled from a fluid-technical point of view with a compressed air unit 9 for the provision of compressed air as a work fluid. In the present configuration, provision is made for the compressed air unit 9 to be included by the console 1. However, this may also vary in alternative configurations and the compressed air unit 9 may be formed at least partly separately from the console 1.

The console 1, in particular the valve unit 3 thereof, is further connected via fluid lines 23, 24 to the vitrectomy cutting tool 2 and in particular to the work chambers 10, 11 there. Consequently, when the vitrectomy cutting tool 2 is connected, the valve unit 3 is able to correspondingly alternately apply compressed air to the work chambers 10, 11. The fluid lines 23, 24 may be at least partly embodied as flexible lines. Moreover, the fluid lines 23, 24 may also include connection elements, with the result that they may be detachably arranged at least in part. The fluid lines 23, 24 may be formed in one piece or else in multiple pieces.

The valve unit 3 is further connected to a control unit 8 of the console 1 which is in the form of an electronic control unit and which supplies the appropriate electrical switching signals, which will be explained in more detail hereinafter, to the valve unit 3 so that the valve unit 3 applies compressed air to the work chambers 10, 11 via the fluid lines 23, 24 as intended. The figures do not illustrate the possible presence of further lines, which for example may be in the form of fluid lines and/or electrical lines, for example in order to be able to supply an irrigation fluid from the console 1 to the vitrectomy cutting tool 2 and/or in order to be able to drain an aspiration fluid from the vitrectomy cutting tool 2 to the console 1. Moreover, further lines may also be provided, for example electrical lines for the sensor system, further control functions of the vitrectomy cutting tool 2, and/or the like.

Figure 2:
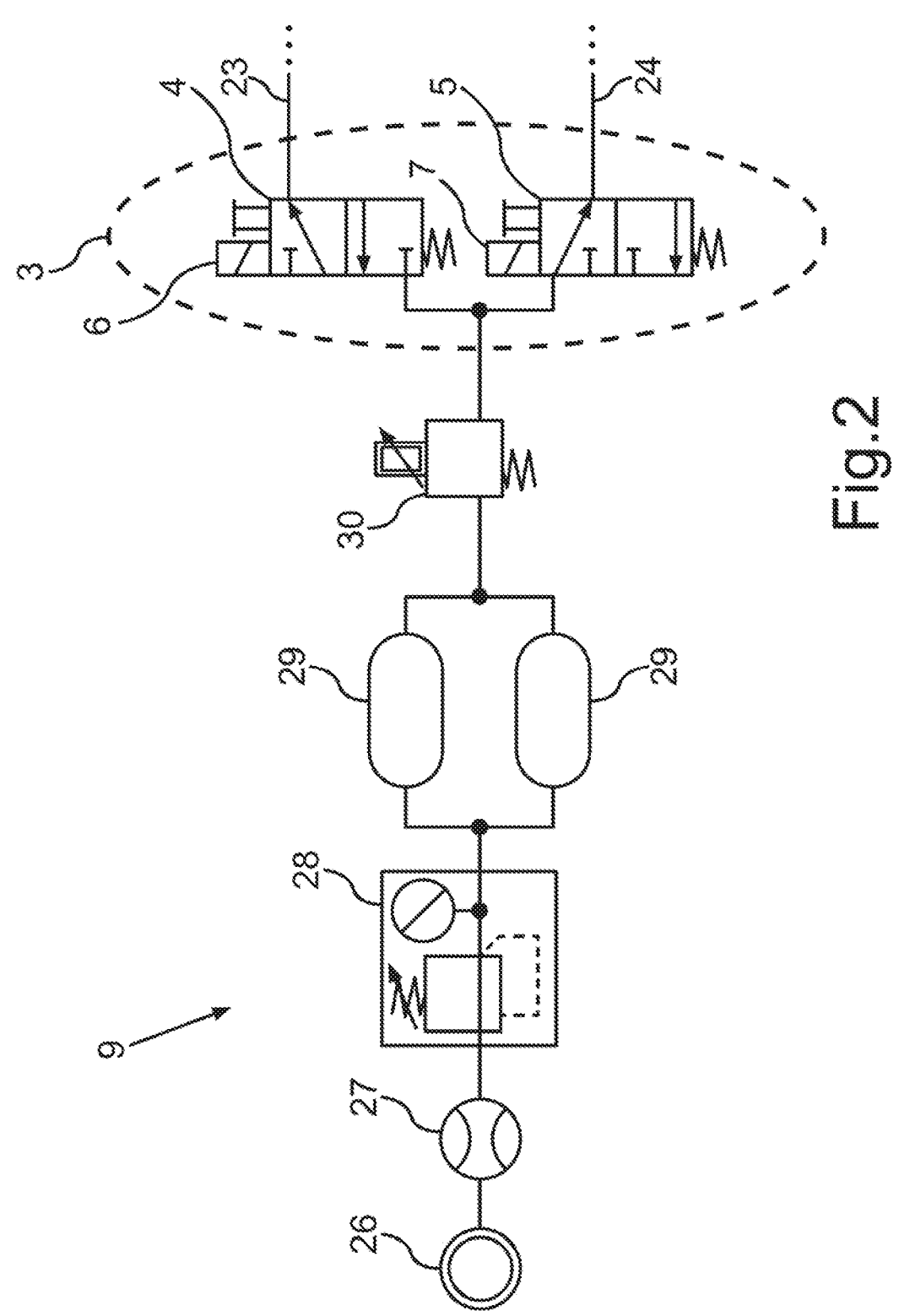
FIG. 2 shows a schematic block diagram of a portion of the console of the ophthalmic surgical system according to FIG. 1, which includes a compressed air unit and a valve unit connected thereto.
Figure 3:
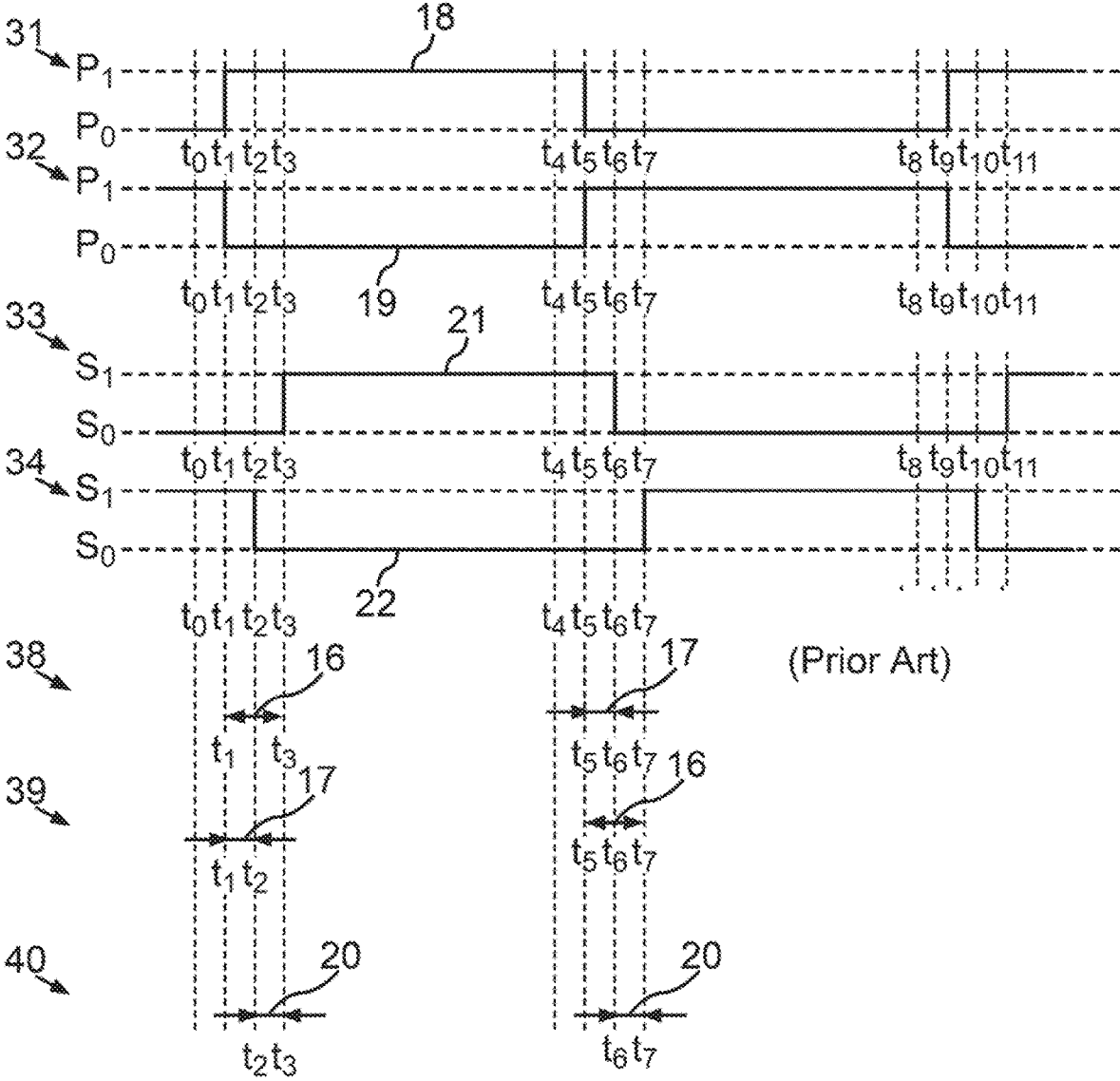
FIG. 3 shows a schematic signal representation of switching signals and switching states of work valves of the valve unit according to FIG. 2.

In a schematic block diagram, FIG. 2 now shows a console 1 portion which includes the compressed air unit 9 and the valve unit 3. As is evident from FIG. 2, the valve unit 3 includes a first work valve 4 for applying compressed air to the first work chamber 10 of the vitrectomy cutting tool 2, depending on a switching state of the first work valve 4. The first work valve 4 includes a first electromagnet 6 as electric drive unit for switching-over the first work valve 4 between a switched-on switching state S1 and a switched-off switching state S0 (FIG. 3). The valve unit 3 further includes a second work valve 5 for applying the compressed air to the second work chamber 11 of the vitrectomy cutting tool 2, depending on a switching state of the second work valve 5. The second work valve 5 includes a second electromagnet 7 as electric drive unit for switching-over the second work valve 5 between a switched-on switching state S1 and a switched-off switching state S0 (FIG. 3). As will be explained below on the basis of FIG. 3, each work valve 4, 5 switches from the switched-off switching state (S0) into the switched-on switching state (S1) during a switch-on time delay 16 and switches from the switched-on switching state (S1) into the switched-off switching state (S0) during a switch-off time delay 17.

The control unit 8 is electrically coupled to the electromagnets 6, 7 and is configured to actuate the electromagnets 6, 7 with respective first and second electrical switching signals 18, 19 such that a respective switching signal 18, 19 successively over time applies a switch-on electric potential P1 for the switched-on switching state S1 and a switch-off electric potential P0 for the switched-off switching state S0 to the respective electromagnet 6, 7 so that the first and the second work valve 4, 5 in each case can alternately adopt the respective switching state. This is evident in diagrams 31 to 34 in a schematic signal representation according to FIG. 3. From this, it is evident that the switching signals 18, 19 for the two electromagnets 6, 7 in each case alternately adopt the switch-on potential P1 and the switch-off potential P0. The electric potential of the switching signals 18, 19 is respectively changed at the times $t_1$, $t_5$. In FIG. 3, this is shown in the two diagrams 31 and 32. Diagram 31 represents a temporal section of the switching signal 18 for the electromagnet 6 and diagram 32 represents a corresponding temporal section of the switching signal 19 for the electromagnet 7.

The electromagnet 6 is actuated such that it switches from the switch-off potential P0 to the switch-on potential P1 at a time $t_1$. This switch-on potential P1 remains up to a time $t_5$. The electromagnet 6 is actuated again at the time $t_5$ such that it switches to the switch-off potential P0. The electromagnet 6 remains at this switch-off potential P0 until it is actuated again at a time $t_9$ and switches to the switch-on potential P1. This curve of a switching signal is denoted by the reference sign 18 in diagram 31.

The electromagnet 7 is actuated substantially simultaneously in a manner analogous thereto. The electromagnet 7 is at the switch-on potential P1 up until the time $t_1$. The electromagnet 7 is actuated at the time $t_1$ and switches to the switch-off potential P0. The electromagnet 7 remains at this switch-off potential P0 until the time $t_5$, when it is actuated again and switches to the switch-on potential P1. This switch-on potential P1 is unchanged up to the time $t_9$. The electromagnet 7 is actuated again at the time $t_9$ and switches to the switch-off potential P0. This curve of a switching signal is denoted by the reference sign 19 in diagram 32.

With the same time scale, diagrams 33 and 34 of FIG. 3 show, assigned in time, the flow-technical switching states S0 and S1 of the work valves 4, 5 using respective graphs 21, 22. The switching states according to the graphs 21, 22 relate to flow-technical switching states, with a value S1 corresponding to the flow-technical switched-on switching state of the respective work valve 4, 5, that is, a compressed air flow is enabled. By contrast, the value S0 is assigned to the flow-technical switched-off switching state, in the case of which the work valve prevents a flow from the compressed air unit 9 to the respective work chamber 10, 11. Consequently, graph 21 is assigned to work valve 4 and graph 22 is assigned to work valve 5.

If the electromagnet 6 is actuated according to the curve of the switching signal 18, then the following profile, represented by a graph 21 in diagram 33, arises for the work valve 4: The electric potential at the electromagnet 6 switches from the switch-off potential P0 to the switch-on potential P1 at the time $t_1$. However, the work valve 4 does not follow this switch instantaneously but rather with a switch-on time delay 16, as shown in diagram 38. This means that the work valve 4 only switches from the switched-off switching state S0 to the switched-on switching state S1 at the time $t_3$. The work valve 4 remains in this switching state. The potential at the electromagnet 6 changes from the switch-on potential P1 to the switch-off potential P0 at the time $t_5$. However, the work valve 4 cannot follow this actuation without delay, but only changes its switching state from S1 to S0 at the time $t_6$. Consequently, there is a switch-off time delay, as illustrated in diagram 38 by reference sign 17. Attention is drawn to the fact that the switch-off time delay 17 is shorter than the switch-on time delay 16 in this embodiment. The work valve 4 initially remains in this switching state S0. The electromagnet 6 is actuated at the time $t_9$ so that the switch-off potential P0 changes to the switch-on potential P1. The work valve 4 then switches its switching state S0 at $t_{11}$, again with the switch-on delay 16, in order to switch to the switching state S1.

This curve is implemented analogously for the work valve 5. If the electromagnet 7 is actuated according to the switching signal 19, then the following switching profile, represented by a graph 22 in diagram 34, arises for the work valve 5: The switching signal of the electromagnet 7 changes from the switch-on potential P1 to the switch-off potential P0 at the time $t_1$. The work valve 5 switches from the switching state S1 to the switching state S0, but not simultaneously at the time $t_1$ and only with a delay at the time $t_2$. Consequently, there is a switch-off time delay 17 (see diagram 39). The work valve 5 initially remains in this switching state S0. The switching state of the electromagnet 7 changes from the switch-off potential P0 to the switch-on potential P1 at the time $t_5$. The work valve 5 does not follow without delay, but only changes its switching state from S0 to S1 at the time $t_7$. Consequently, there is a switch-on time delay 16 (see diagram 39). The work valve 5 initially remains in this switching state S1. The electromagnet 7 is actuated at the time $t_9$ so that the switch-on potential P1 changes to the switch-off potential P0. The work valve 5 then switches its switching state S1 at $t_{10}$ with the switch-off time delay 17, in order to switch back to the switching state S0.

In the present configuration, provision is further made for the work valves 4, 5 to allow a drainage of compressed air from the respective work chambers 10, 11 in the respective switched-off switching state. However, this may also be constructed differently in alternative configurations. By way of example, separate release valves may be provided for draining the compressed air from the work chambers 10, 11, in order to enable a drainage of the compressed air from the work chambers 10, 11.

As is evident from diagram 40 in FIG. 3, there are time periods which arise on account of the switching time delays of the work valves 4, 5 and during which both work valves 4, 5 are simultaneously in the switched-off switching state. In the present case, this situation is present in a time period between $t_2$ and $t_3$, in a time period between $t_6$ and $t_7$, and in a time period from $t_{10}$ to $t_{11}$. In the present configuration, this arises because the switch-on time delay 16, that is, for example the time period between $t_1$ and $t_3$, is longer than the switch-off time delay 17, that is, for example the time period between $t_5$ and $t_6$. In the present case, provision is made for the work valves 4, 5 to have substantially the same embodiment. The time periods in which both work valves 4, 5 are simultaneously in the switched-off state were found to be disadvantageous, especially in the case of a high cycle rate of the vitrectomy cutting tool 2, as already explained above.

Improvements in the functionality of the ophthalmic surgical system 100, in particular in relation to vibrations, acoustic noise, a maximum attainable cycle rate, and more, are addressed here by the disclosure by virtue of reducing the length of time of the aforementioned time periods in which both work valves 4, 5 simultaneously are in the switched-off switching state. The disclosure achieves this by virtue of the control unit 8 being configured to bring about a switch of a switching signal 18, 19, assigned to the respective work valve 4, 5, from the switch-off potential P0 to the switch-on potential P1 during a difference time period 20 if—as in the present case—the switch-on time delay 16 of the respective work valve 4, 5 is longer than the switch-off time delay 17 of the respective other work valve 4, 5. This is schematically illustrated below on the basis of FIG. 4, which shows a schematic signal representation like in FIG. 3. To simplify the temporal assignment in relation to the representation according to FIG. 3, FIG. 4 likewise includes diagrams 31 and 33 as a reference. A length of time of the difference time period 20 arises on the basis of a time difference between the switch-on time delay 16 of the respective work valve 4, 5 and the switch-off time delay 17 of the respective other work valve 4, 5. This is evident from a diagram 40 in FIG. 3. Accordingly, the length of time of the difference time period for example emerges from a difference of the times $t_3$ minus $t_2$, $t_2$ minus $t_6$, and so on.

Figure 4:
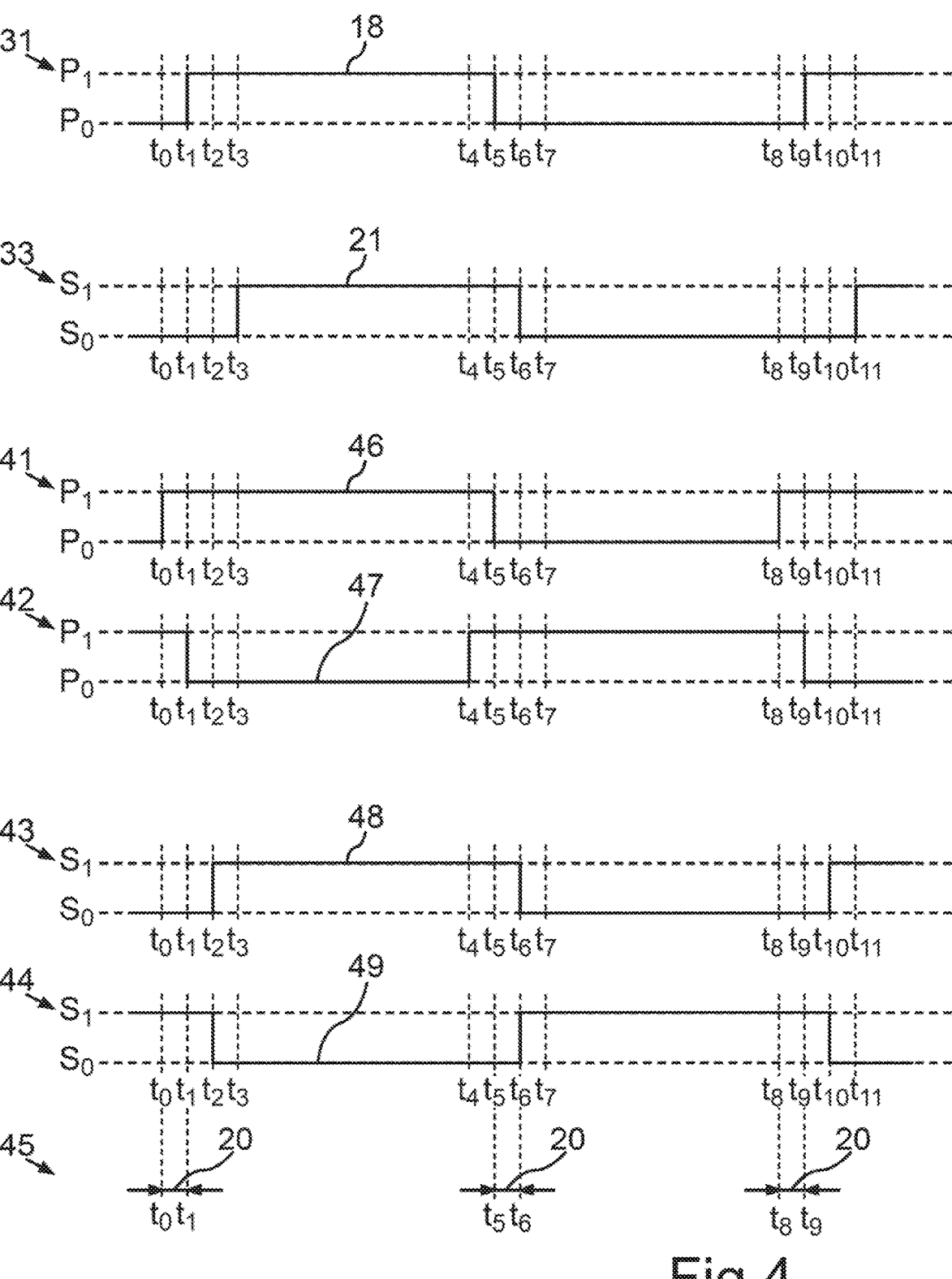
FIG. 4 shows a schematic signal representation like in FIG. 3, in which the switching signals partially overlap in time by a difference time period.

In a diagram 41 according to FIG. 4, which has the same time axis as diagram 31, a graph 46 represents a switching signal for the first electromagnet 6. In comparison with the first switching signal according to the graph 18 in diagram 31, the switching signal according to the graph 46 assumes the potential P1 for a time lengthened by the difference time period 20. Since a period duration of the first switching signal remains constant, the time period during which the first switching signal adopts the potential P0 has been shortened accordingly by the difference time period 20. That is, the first switching signal according to the graph 46 already switches from the potential P0 to the potential P1 at the time to, and maintains this potential until the time $t_5$. The switch at this time corresponds to the switch according to the graph 18. At the time $t_5$ the first switching signal switches again, from the potential P1 to the potential P0, and keeps this latter potential until a time $t_8$, when there is another change from the potential P0 to the potential P1. This continues accordingly over time.

Something corresponding arises for the associated second switching signal for the electromagnet 7, which is represented on the basis of a graph 47 in a diagram 42 of FIG. 4 with the same time axis as the diagram 41. According to the graph 47, the second switching signal switches from the potential P1 to the potential P0 at the time $t_1$ and maintains this potential up to a time $t_4$. At the time $t_4$, the second switching signal switches from the potential P0 to the potential P1 and maintains this potential up to a time $t_9$. There is a change from the potential P1 to the potential P0 at the time $t_9$. This likewise continues accordingly over time.

Diagrams 43 and 44 illustrate the associated switching states of the work valves 4, 5 by way of respective graphs 48, 49. The diagrams 43 and 44 have the same time axis as the respectively assigned diagrams 41 and 42. Taking account of the switching time delays 16, 17 of the work valves 4, 5, the flow-technical switching states arise as follows: As is evident from the graph 48, the switching state of the work valve 4 switches from the switched-off switching state to the switched-on switching state at the time $t_2$ and remains in this switching state up to the time $t_6$. There is another switch in the switching state at the time $t_6$, to be precise from the switched-on switching state to the switched-off switching state, and this switching state is maintained up until time $t_{10}$. At the time $t_{10}$, the switching state changes again from the switched-off switching state to the switched-on switching state. This continues accordingly over time, based on the first switching signal according to the graph 46.

As is evident from the graph 49, the switching state of the work valve 5 switches from the switched-on switching state to the switched-off switching state at the time $t_2$ and remains in this switching state up to the time $t_6$. There is another switch in the switching state at the time $t_6$, to be precise from the switched-off switching state to the switched-on switching state, and this switching state is maintained up until time $t_{10}$. At the time $t_{10}$, the switching state changes again from the switched-on switching state to the switched-off switching state. This continues accordingly over time, based on the second switching signal according to the graph 47.

As is evident on the basis of a diagram 45 in FIG. 4, the difference time periods 20 in which the two switching signals simultaneously have the potential P1 arise for both switching signals according to the graphs 46 and 47, for example in the difference time period 20 which is bounded by the times to and $t_1$, in the difference time period 20 which is bounded by the times $t_5$ and $t_6$, and in the difference time period 20 which is bounded by the times $t_{10}$ and $t_{11}$. This likewise continues accordingly over time. What arises on the basis of the graphs 48 and 49 from diagrams 43 and 44 is that, if the difference time periods 20 are fully exploited, the flow-technical switching states of the work valves 4, 5 switch substantially simultaneously, to be precise at the times $t_2$, $t_6$, and $t_{10}$. The switching states arising on the basis of the diagrams 33 and 34 in FIG. 3, in which both work valves 4, 5 are simultaneously in the switched-off switching state, to be precise for example in the time period bounded by the times $t_2$ and $t_3$ or by the times $t_6$ and $t_2$, can be largely avoided as a result.

The difference time period 20 need not be exploited in full so that the time periods during which both work valves 4, 5 simultaneously are in the switched-off switching state can be reduced according to need. In principle, there is the option of letting the time periods during which both work valves 4, 5 are simultaneously in the switched-off switching state become virtually zero by way of the full exploitation of the difference time period 20. From this, it is evident that the switched-on switching state of the work valves 4, 5 can be lengthened significantly using the disclosure by exploiting the difference time periods 20. As a result, it is also possible to increase a pressure difference between the work chambers 10, 11 of the vitrectomy cutting tool 2 during intended operation. This makes it possible to be able to reach a higher maximum attainable cycle rate and/or allows a pressure of the compressed air unit 9 to be reduced, in order to be able to reduce for example acoustic noise and vibrations in this way. Overall, it is consequently possible to improve the intended operation of the ophthalmic surgical system 100.

Should the switch-on time delay 16 be shorter than the switch-off time delay 17, then the control unit 8 can be configured to delay the switch at least by the difference time period 20. This can also achieve reliable functionality. This is not illustrated in the figures, however.

Further, a schematic structure of the compressed air unit 9 is evident from FIG. 2. The compressed air unit 9 includes a compressed air connection 26 to an external compressed air source (not depicted in any more detail). Connected to the compressed air connection 26 is a flow sensor 27 which is able to detect a flow of compressed air and which supplies a corresponding sensor signal to the control unit 8. Further, connected to the flow sensor 27 is a source pressure controller 28 which in the present configuration reduces a pressure of the external compressed air source to a maximum operating pressure of the console 1 or ophthalmic surgical system 100, and which supplies the compressed air to two tanks 29. Further, connected to the tanks 29 is a proportional valve 30, via which the compressed air from the tanks 29 can be supplied to the valve unit 3. Even if two tanks 29 are depicted in the present case, the disclosure is not restricted thereto. In principle, it is also possible to provide merely one tank 29. The proportional valve 30 is likewise connected to the control unit 8 so that it is possible to set a desired operating pressure or work pressure of the compressed air for the operation of the ophthalmic surgical system 100.

Figure 5:
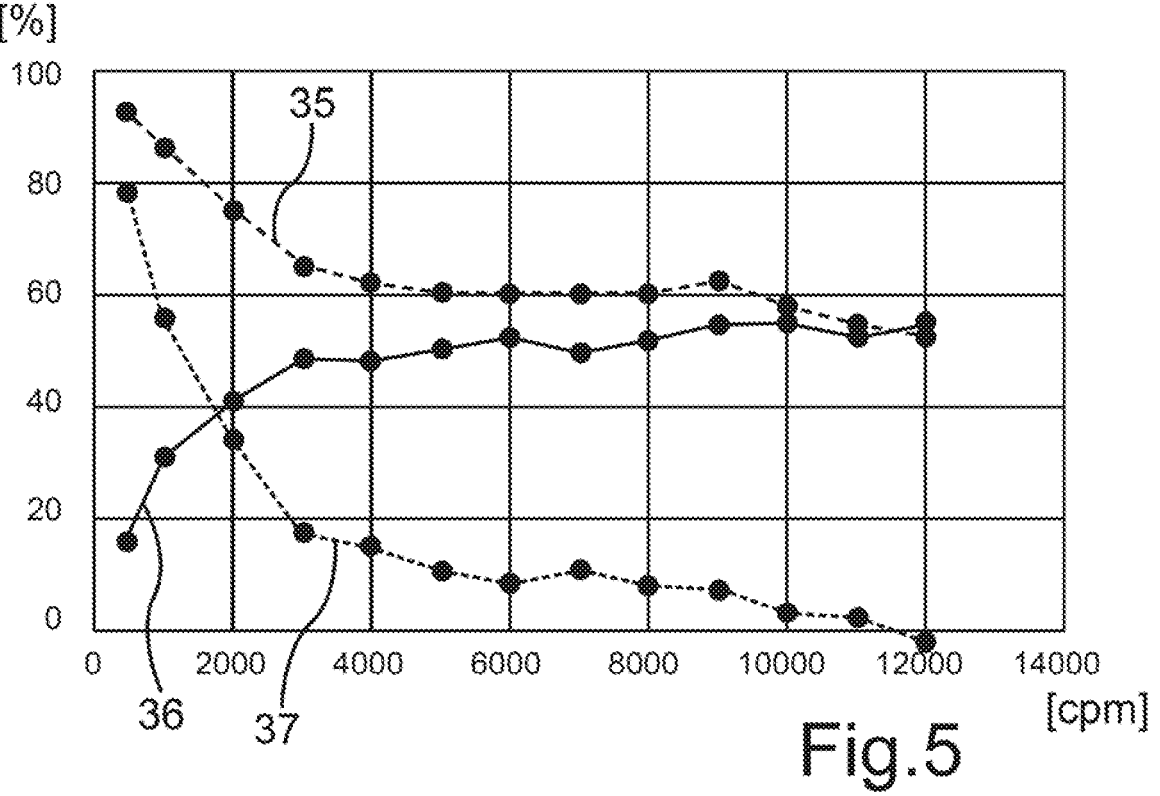
FIG. 5 shows a schematic diagram representation of a duty cycle of the switching signals according to FIG. 2, depending on a cycle rate of the vitrectomy cutting tool, for a first air pressure; and, FIG. 6 shows a schematic diagram representation like in FIG. 5 for a second air pressure.
Figure 6:
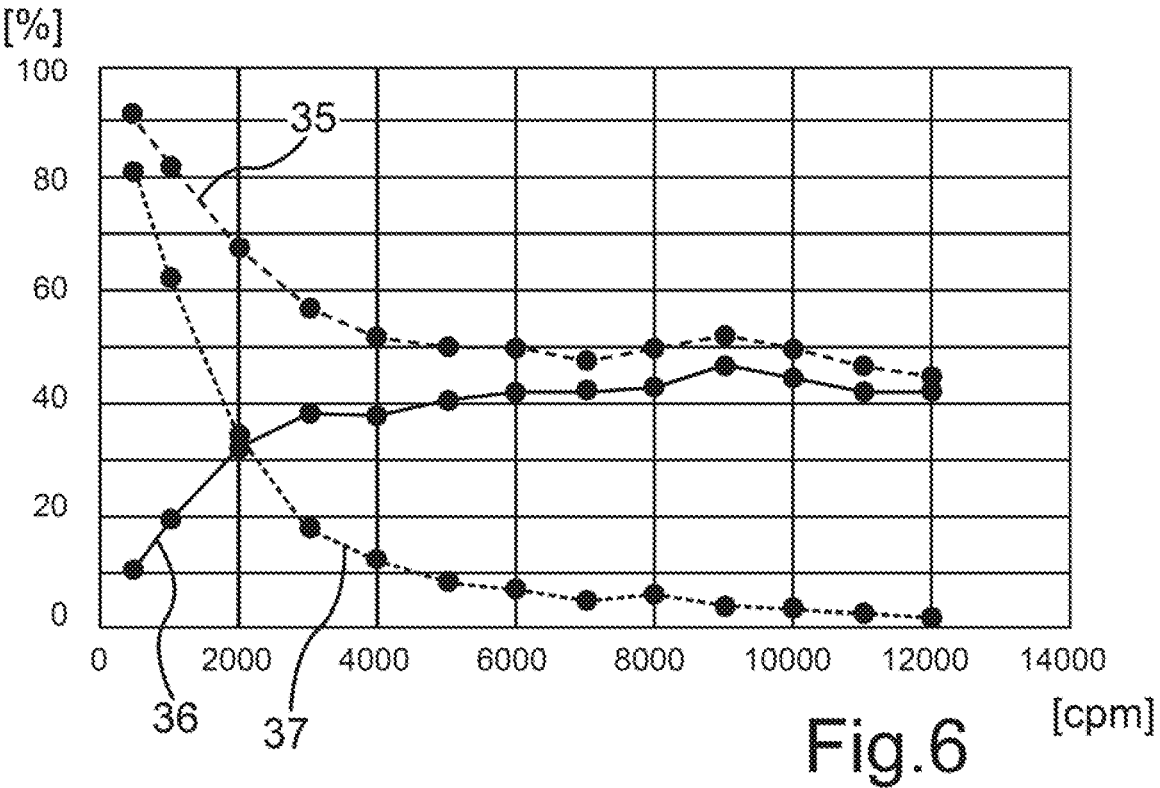

FIGS. 5 and 6 show examples of duty cycles of the switching signals 18, 19 as a function of a cycle rate. An ordinate is assigned to a relative duty cycle in %, whereas an abscissa is assigned to the cycle rate in cycles per minute (cpm). In FIG. 5, an operating pressure of the compressed air is approximately 1.5 bar in the present configuration. A graph 35 represents a maximum duty cycle, for which the vitrectomy cutting tool 2 is fully opened. A graph 36 represents a smallest duty cycle for the vitrectomy cutting tool 2, in the case of which the vitrectomy cutting tool 2 closes completely. Consequently, a complete cutting cycle is provided for duty cycles between the graphs 35 and 36. A graph 37 represents the difference of the graphs 35 and 36. As is evident from FIG. 5, the range of selectable duty cycles for a certain cycle rate reduces with increasing cycle rate. The maximum possible cycle rate for this embodiment has been reached at a cycle rate of approximately 11 500 cpm. A variation of the duty cycle is no longer possible here.

FIG. 6 shows a corresponding representation to FIG. 5, with the operating pressure however being approximately 1.8 bar in this case. It is evident that the maximum possible cycle rate has not yet been reached even at 12 000 cpm. Thus, it is still possible to adjust the duty cycle within the aforementioned limits even at a cycle rate of 12 000 cpm, albeit with a comparatively small adjustable range in the present case, which is merely approximately 3 to 4% at 12 000 cpm. From this, it is evident that it is also possible to realize an increase in the maximum attainable cycle rate by increasing the operating pressure. By the additional application of the disclosure, as explained above, this can be further improved because the differential pressure can be further improved by better exploitation of the switching properties of the work valves 4, 5.

It is understood that the foregoing description is that of the preferred embodiments of the invention and that various changes and modifications may be made thereto without departing from the spirit and scope of the invention as defined in the appended claims.

1 Console
2 Vitrectomy cutting tool
3 Valve unit
4 Work valve
5 Work valve
6 Electromagnet
7 Electromagnet
8 Control unit
9 Compressed air unit

10 Work chamber
11 Work chamber
12 Drive piston
13 Work cylinder
14 Drive rod
15 Cutting unit
16 Switch-on time delay
17 Switch-off time delay
18 Electrical switching signal
19 Electrical switching signal
20 Difference time period
21 Switching state
22 Switching state
23 Fluid line
24 Fluid line
26 Compressed air connection
27 Flow sensor
28 Source pressure controller
29 Compressed air tank
30 Proportional valve
31 Diagram
32 Diagram
33 Diagram
34 Diagram
35 Graph
36 Graph
37 Graph
38 Diagram
39 Diagram
40 Diagram
41 Diagram
42 Diagram
43 Diagram
44 Diagram
45 Diagram
46 Graph
47 Graph
48 Graph
49 Graph
P1 Switch-on electric potential
P0 Switch-off electric potential
S1 Pneumatic switch-on state
S0 Pneumatic switch-off state

The invention claimed is:

1. A console for an ophthalmic surgical system for operating a handpiece which is drivable via a work fluid, the handpiece being suitable for use in an ophthalmic surgical method for treating an eye, the console comprising:

a first work valve for applying the work fluid to a first work chamber of the handpiece in dependence upon a switching state of said first work valve, said first work valve including a first electric drive unit configured to switch said first work valve between a switched-on switching state and a switched-off switching state;

a second work valve for applying the work fluid to a second work chamber of the handpiece in dependence upon a switching state of said second work valve, said second work valve including a second electric drive unit configured to switch said second work valve between a switched-on switching state and a switched-off switching state;

each of said first work valve and said second work valve being configured to switch from the switched-off switching state to the switched-on switching state during a switch-on time delay and to switch from the switched-on switching state to the switched-off switching state during a switch-off time delay;

a control unit electrically coupled to said first electric drive unit and to said second electric drive unit and configured to actuate said first electric drive unit via a first electrical switching signal and said second electric drive unit via a second electrical switching signal such that a corresponding one of said first electrical switching signal and said second electrical switching signal successively over time applies a switch-on electric potential for the switched-on switching state and a switch-off electric potential for the switched-off switching state to a corresponding one of said first electric drive unit and said second electric drive unit so that said first work valve and said second work valve in each case alternately adopt the switched-on and the switched-off switching state, wherein in relation to a respective change of the switching states of said first work valve and said second work valve, said control unit is configured such that:

said first electrical switching signal and said second electrical switching signal assigned to corresponding ones of said first work valve and said second work valve at least intermittently adopt the switch-on electric potential concurrently during a difference time period if the switch-on time delay of said first work valve and said second work valve is longer than the switch-off time delay of said first work valve and said second work valve, or said first electrical switching signal and said second electrical switching signal assigned to corresponding ones of said first work valve and said second work valve at least intermittently adopt the switch-off electric potential concurrently during the difference time period if the switch-on time delay of said first work valve and said second work valve is shorter than the switch-off time delay of said first work valve and said second work valve; and, wherein the length of time of the difference time period arises on a basis of a difference between the switch-on time delay of said first work valve and said second work valve and the switch-off time delay of said first work valve and said second work valve.

2. The console of claim 1, wherein the console is configured to drain the work fluid from a corresponding one of the first work chamber and the second work chamber in the switched-off switching state of the correspondingly assigned one of said first work valve and said second work valve.

3. The console of claim 2, wherein the work fluid is drained via a corresponding one of said first work valve and said second work valve.

4. The console of claim 2, wherein the work fluid is drained via a corresponding first or second release valve.

5. The console of claim 1, wherein said control unit is configured to determine the length of time of the difference time period independently of a frequency of said first electrical switching signal and said second electrical switching signal.

6. The console of claim 1, wherein for a purpose of determining the switch-on time delay or switch-off time delay of a respective one of said first work valve and said second work valve, said control unit is configured to detect a handpiece-side pressure of the work fluid via a corresponding pressure sensor at said first work valve and said second work valve.

7. The console of claim 1, wherein said control unit is configured to detect, via a position sensor, at least one end position of a drive piston movably arranged between the first work chamber and the second work chamber, and to additionally adjust said first and second electrical switching signals on a basis of the at least one detected end position.

8. The console of claim 1, wherein said handpiece is a vitrectomy cutting tool and said control unit is configured to additionally determine a duty cycle of said first and said second electrical switching signals for a specified cycle rate, at least on a basis of the specified cycle rate, a maximum cycle rate and the switch-on time delay or switch-off time delay of said first and second work valves.

9. The console of claim 1, wherein said control unit is configured to additionally determine a duty cycle of said first and second electrical switching signals for a specified or specifiable cycle rate, at least on the basis of a period duration of the specified or specifiable cycle rate, a period duration of a maximum cycle rate and the switching time delays of said first and second work valves.

10. An ophthalmic surgical system comprising:

a handpiece configured to be driven via a work fluid;

said handpiece having a first work chamber, a second work chamber, and a drive piston;

said drive piston being movably arranged between said first work chamber and said second work chamber and wherein the work fluid from said first and said second work chambers is applicable to said drive piston;

a console for coupling said first work chamber and said second work chamber with the work fluid and for applying the work fluid to said first work chamber and said second work chamber;

a work fluid source for providing the work fluid;

said console having a first work valve, a second work valve, and a control unit;

said first work valve being configured to apply the work fluid to said first work chamber of said handpiece in dependence upon a switching state of said first work valve, said first work valve including a first electric drive unit configured to switch said first work valve between a switched-on switching state and a switched-off switching state;

said second work valve being configured to apply the work fluid to said second work chamber of said handpiece in dependence upon a switching state of said second work valve, said second work valve including a second electric drive unit configured to switch said second work valve between a switched-on switching state and a switched-off switching state;

each of said first work valve and said second work valve being configured to switch from the switched-off switching state to the switched-on switching state during a switch-on time delay and to switch from the switched-on switching state to the switched-off switching state during a switch-off time delay;

said control unit being electrically coupled to said first electric drive unit and to said second electric drive unit and configured to actuate said first electric drive unit via a first electrical switching signal and said second electric drive unit via a second electrical switching signal such that a corresponding one of said first electrical switching signal and said second electrical switching signal successively over time applies a switch-on electric potential for the switched-on switching state and a switch-off electric potential for the switched-off switching state to a corresponding one of said first electric drive unit and said second electric drive unit so that said first work valve and said second work valve in each case alternately adopt the switched-on and the switched-off switching state, wherein in relation to a respective change of the switching states of said first work valve and said second work valve, said control unit is configured such that said first electrical switching signal and said second electrical switching signal assigned to corresponding ones of said first work valve and said second work valve at least intermittently adopt the switch-on electric potential concurrently during a difference time period if the switch-on time delay of said first work valve and said second work valve is longer than the switch-off time delay of said first work valve and said second work valve, or such that said first electrical switching signal and said second electrical switching signal assigned to corresponding ones of said first work valve and said second work valve at least intermittently adopt the switch-off electric potential concurrently during the difference time period if the switch-on time delay of said first work valve and said second work valve is shorter than the switch-off time delay of said first work valve and said second work valve; and, wherein the length of time of the difference time period arises on a basis of a difference between the switch-on time delay of said first work valve and said second work valve and the switch-off time delay of said first work valve and said second work valve.

11. The ophthalmic surgical system of claim 10, wherein said handpiece is configured for ophthalmic surgical methods for treating an eye.

\* \* \* \* \*